United States Patent [19]

Jarvik

[11] Patent Number: 5,613,935
[45] Date of Patent: Mar. 25, 1997

[54] HIGH RELIABILITY CARDIAC ASSIST SYSTEM

[76] Inventor: Robert Jarvik, 124 W. 60th St., New York, N.Y. 10023

[21] Appl. No.: 357,456

[22] Filed: Dec. 16, 1994

[51] Int. Cl.$^6$ ................................................. A61F 1/24
[52] U.S. Cl. ........................................................ 600/16
[58] Field of Search ............................ 600/16; 607/33; 128/903; 604/151

[56] References Cited

U.S. PATENT DOCUMENTS

| | | | |
|---|---|---|---|
| 4,134,408 | 1/1979 | Brownlee et al. | 607/33 |
| 4,507,048 | 3/1985 | Belenger et al. | 415/90 |
| 4,625,712 | 12/1986 | Wampler . | |
| 4,704,121 | 11/1987 | Moise | 623/3 |
| 4,763,660 | 8/1988 | Kroll et al. . | |
| 4,846,152 | 7/1989 | Wampler et al. | 600/15 |
| 4,957,504 | 9/1990 | Chardack | 623/3 |
| 4,994,017 | 2/1991 | Yozu | 600/16 |
| 4,994,078 | 2/1991 | Jarvik | 623/3 |
| 5,049,134 | 9/1991 | Golding et al. | 604/151 |
| 5,092,879 | 3/1992 | Jarvik | 623/3 |
| 5,112,200 | 5/1992 | Isaacson et al. | 417/356 |
| 5,147,388 | 9/1992 | Yamazaki | 623/2 |
| 5,211,546 | 5/1993 | Isaacson et al. | 417/356 |
| 5,317,220 | 5/1994 | Godkin | 310/12 |
| 5,324,177 | 6/1994 | Golding et al. | 417/423 |
| 5,350,413 | 9/1994 | Miller | 607/61 |
| 5,370,509 | 12/1994 | Golding et al. | 417/723 |

*Primary Examiner*—Marvin M. Lateef
*Assistant Examiner*—Scott M. Getzow

[57] ABSTRACT

A high reliability cardiac assist system is provided for permanent use. An electric motor having dual sets of coils rotates the impeller of an intraventricular axial flow pump in the preferred embodiment. The dual motor coils are powered by separate redundant battery and electronics systems configured such that if any wire breaks or if any electrical system component fails the pump will continue to run and sustain the life of the patient powered by the other electronics and battery system. High reliability pump bearings, pump structure to prevent failure due to thrombus, high reliability power cable conduits and connectors, high reliability redundant transcutaneous power transmission systems, and other sub-systems are provided which interact together in an integrated fashion to permit function for more than a decade following surgical implantation of the system without re-operation.

36 Claims, 7 Drawing Sheets

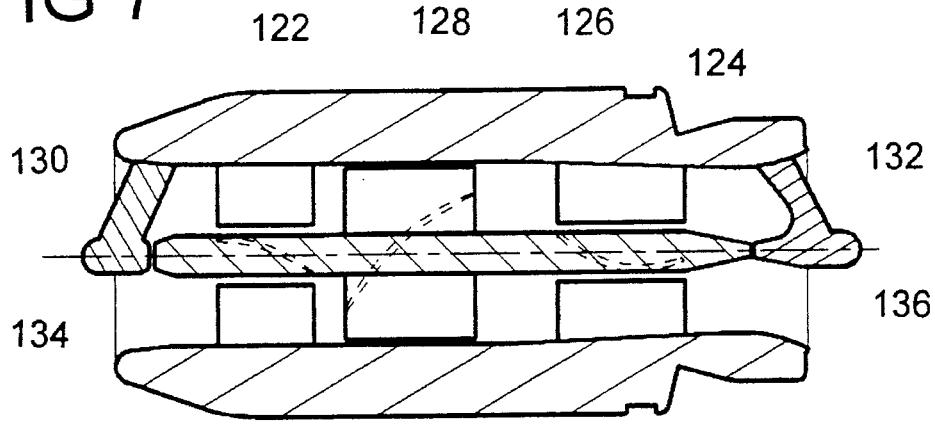
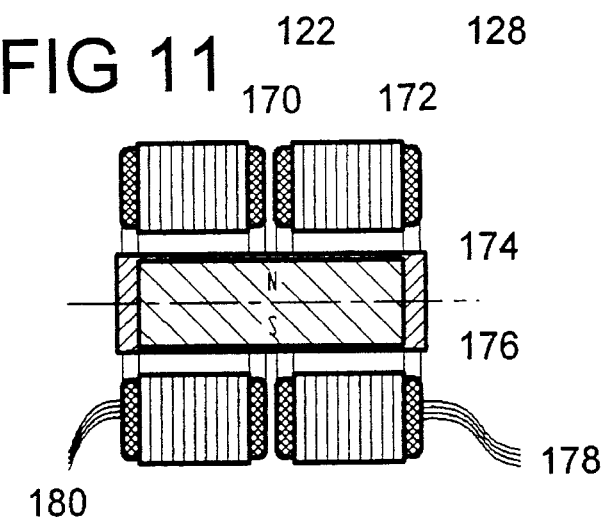
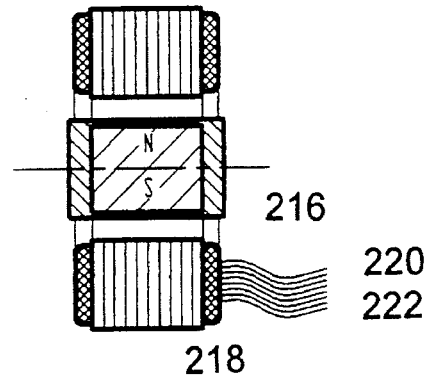
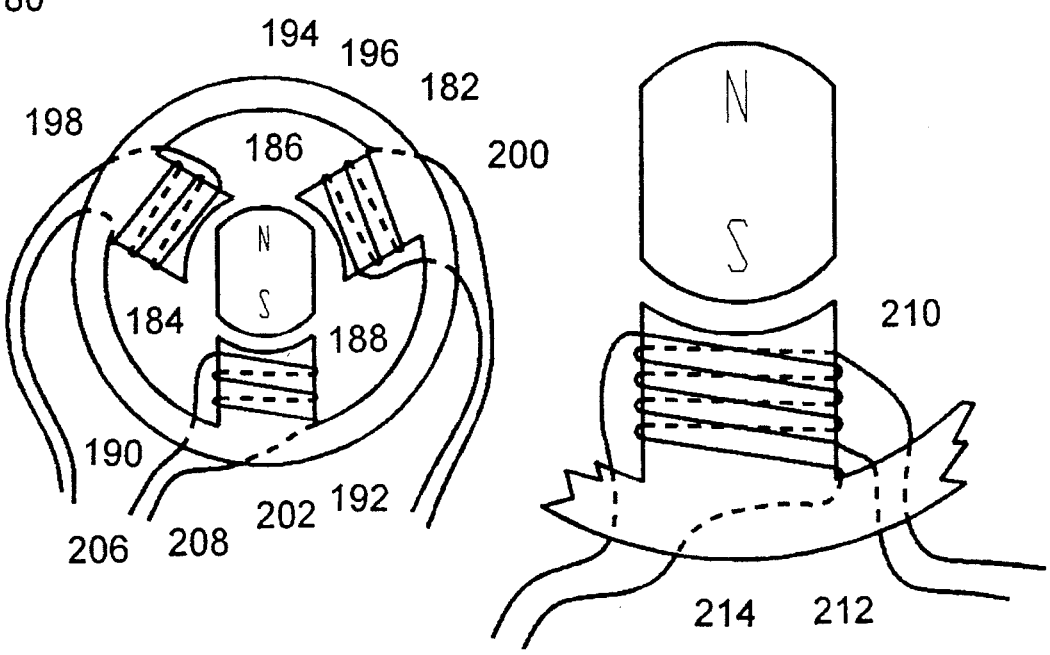

HIGH RELIABILITY CARDIAC ASSIST SYSTEM

BACKGROUND

Long term intraventricular cardiac assist devices are blood pumps that are surgically implanted within the diseased natural heart to support its function for extended periods of time. They must be miniaturized and must be extremely reliable. Blood pumps capable of this are disclosed in my U.S. Pat. No's. 4,994,078 and 5,092,879 entitled "Intraventricular Artificial Hearts and Methods of their Surgical Implantation and Use". Four-month animal survival with these devices is reported by Macris, et al., in the American Society of Artificial Organs Proceedings for 1994. Bearing durability in excess of twenty billion revolutions has been achieved in bench tests which represents about five years of pumping at 9,000 RPM. Wear measurements of bearings after five months' implantation in a calf indicate virtually no wear with projected bearing life in excess of 20 years. These findings prove that the intraventricular approach is likely to succeed.

OBJECTS OF THE INVENTION

The object of the present invention is to provide a complete cardiac assist system including not only the blood pump and motor controller, but also all of the ancillary components that are required to provide the patient with full mobility and a high quality of life. In Table 1 of U.S. Pat. No. 4,994,078 I identified transcutaneous intraventricular electric circulatory support systems as the best overall among numerous types of configurations based on availability, hemodynamic function, thrombus risk, system reliability, infection/rejection, quality of life, and cost. The object of the present invention is to provide exactly such a complete system.

Further objects of the present invention are:

1. To provide backup and redundant components which improve system safety and reliability including;
   a. Dual motor windings with dual sets of motor power wires such that if any wire breaks the pump will continue to run,
   b. Dual motor control electronics adapted to maintain operation of the pump in the event of failure of any electronics component,
   c. Dual battery power systems adapted to maintain power to the pump in the event of failure of either one,
   d. Dual sets of transcutaneous power transmission transmitter and receiver coils, permitting continued operation in the event of failure of either, and also permitting only one set to be used at a time to intermittently relieve pressure on the skin and thereby avoid tissue damage,
   e. A backup valve in the outflow graft such that if the pump stops for any reason the valve will prevent aortic regurgitation and permit the residual function of the natural heart to sustain the life of the patient while the device can be repaired or replaced,
   f. Implantable power cable connectors permitting replacement of components in the event of failure or when the components are worn out (such as implanted batteries), without requiring replacement of the entire system,
2. To provide thin curved battery packs worn by the patient in a "shoulder pad" configurations,
3. To provide thin curved internal battery packs implanted in the patient in place of removed ribs,
4. To provide flexible power cable conduits interconnecting the implanted components which utilize metal bellows to permit complete hermetic sealing of the pump motor and electronics,
5. To provide a control system which intermittently reduces the motor speed enough to reduce pump outflow pressure below aortic pressure, thereby causing the prosthetic valve to close and thereby helping to prevent valve thrombus,
6. To provide a control system utilizing sensors to recognize whether the patient is upright or recumbent and to adjust the pump flow according to this and other information about the patient's hemodynamic requirements,
7. To provide improved blood-immersed bearings for rotary blood pumps, and,
8. To provide improved means of providing high flow washing of blood- immersed bearings and thereby prevent failure of the pump due to thrombus accumulation.

THE FIGURES

FIG. 7 is a longitudinal section of a generalized pump design having both inflow and outflow stators.

FIG. 11 is a longitudinal section of a motor set using dual armatures and a single rotor.

FIG. 12 is a schematic illustration of the laminations, windings, and rotor magnet of a three-phase motor.

FIG. 13 is a detail of the windings of a motor similar to that shown in FIG. 12 in which two sets of coils are utilized.

FIG. 14 is a longitudinal section of a motor having two sets of coils like that shown in FIG. 13.

Figure 18A:
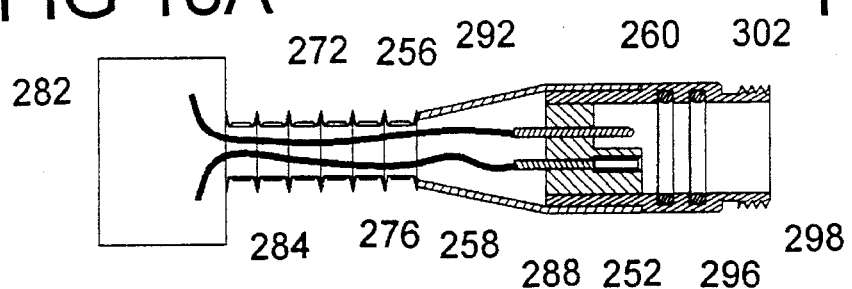

FIGS. 18A & B are partially schematic longitudinal sections of two hermetically sealed electronics enclosures, metal bellows power conduits and wires within them, and the male and female sides of an implantable connector.

Figure 18C:
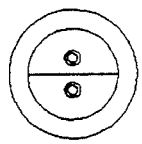

FIG. 18C is an end view of the connector shown in FIG. 18A.

Figure 19:
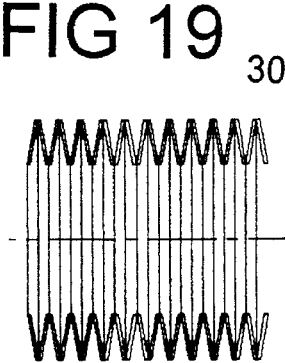

FIG. 19 is a longitudinal section of a standard metal bellows.

Figure 20:
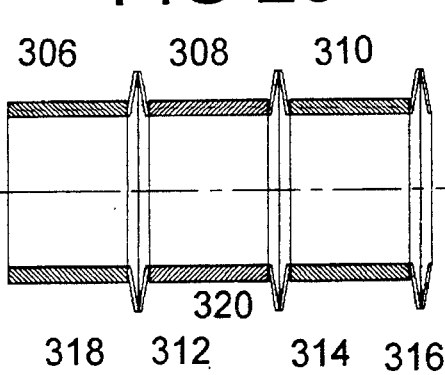
Figure 21:
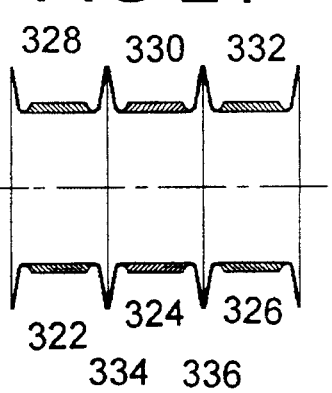
Figure 1:
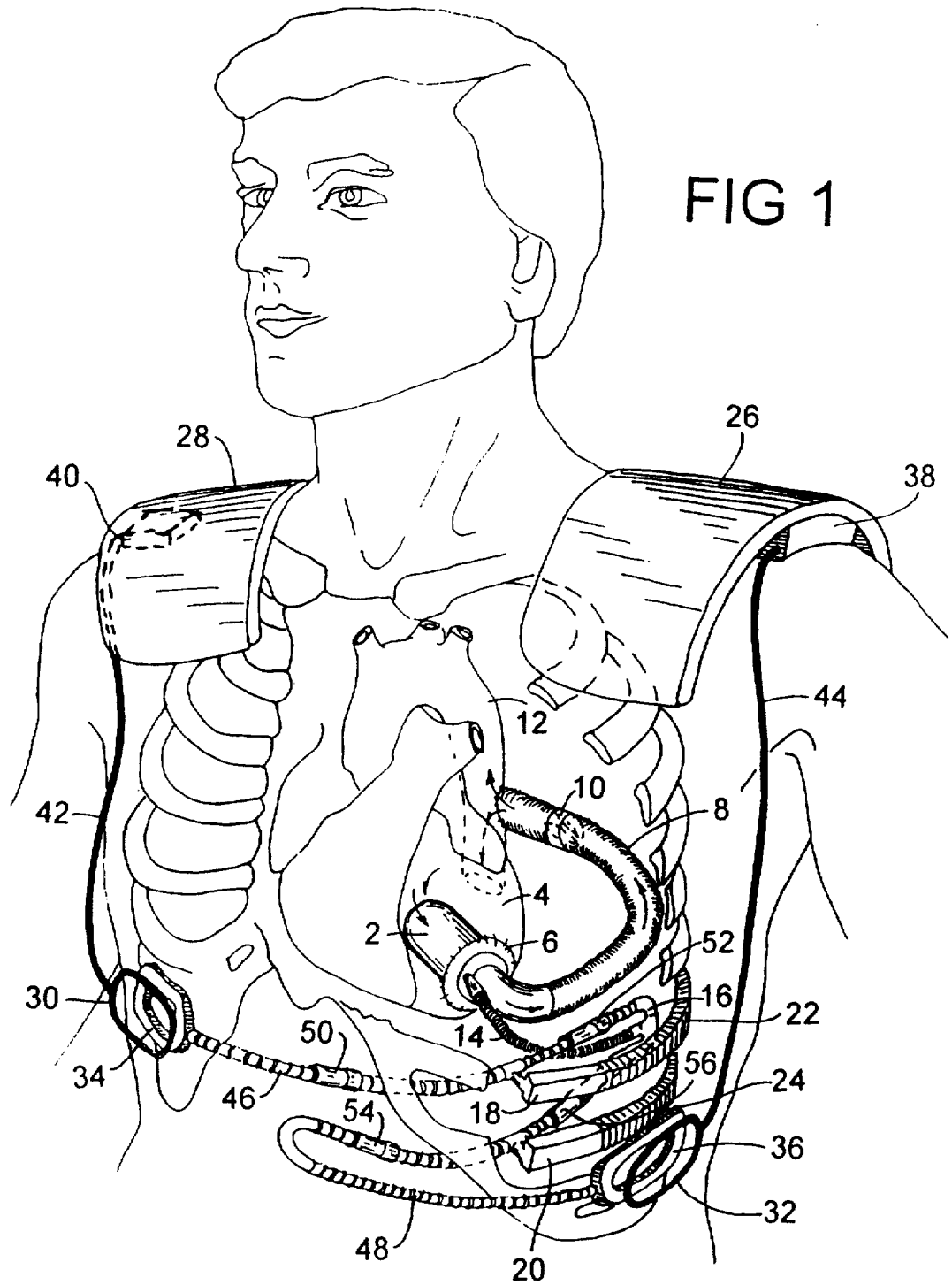
Figure 2:
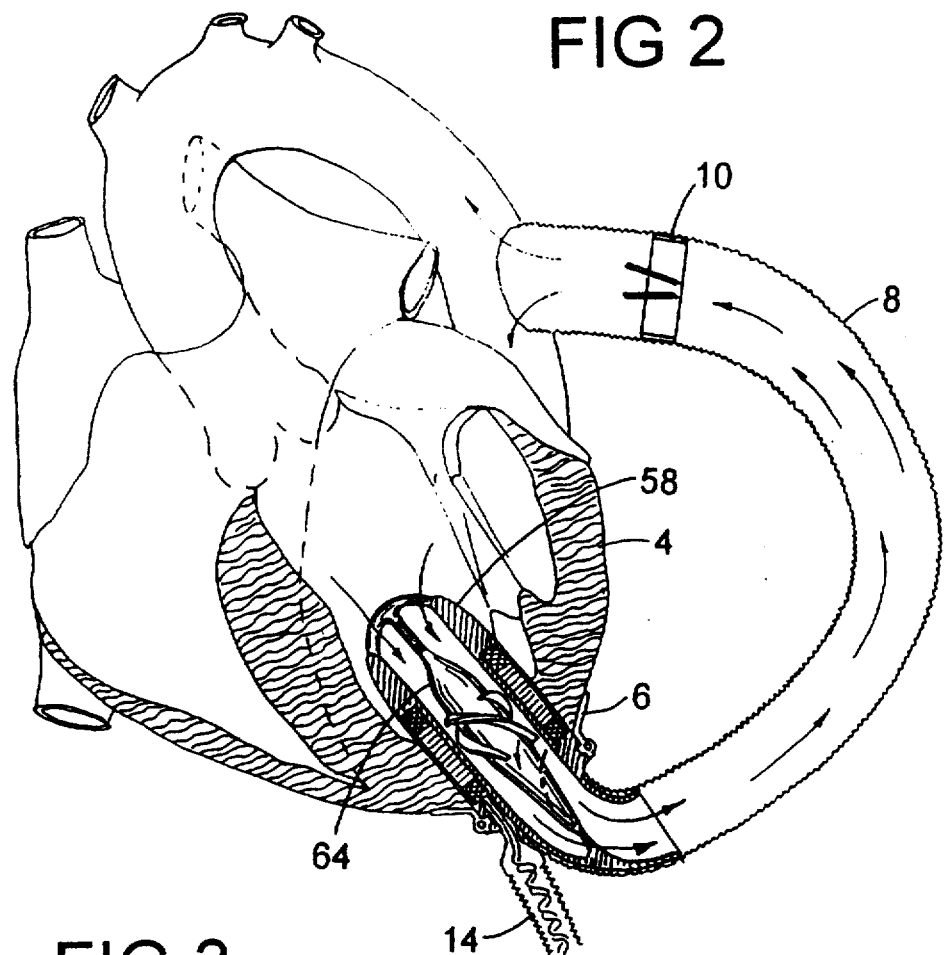
Figure 3:
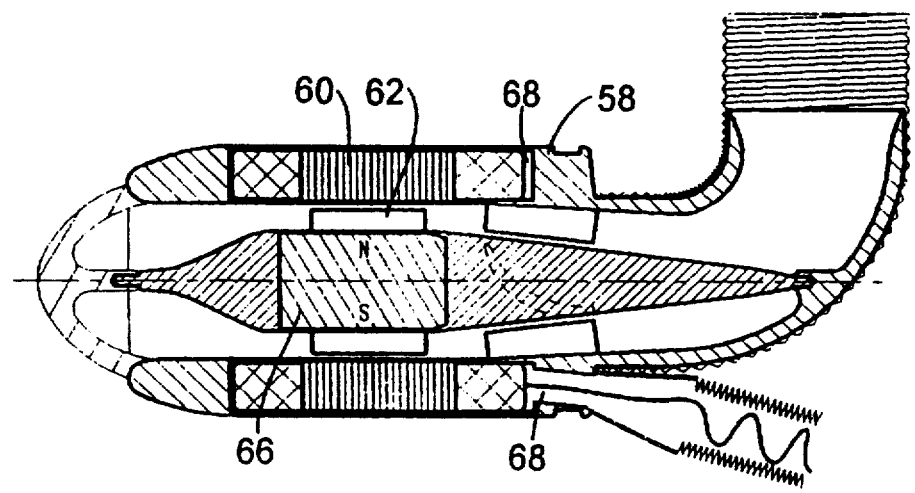
Figure 4:
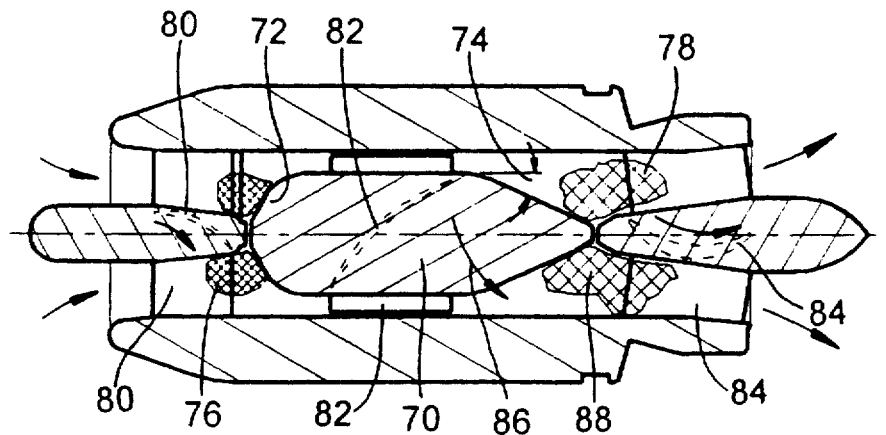
Figure 5:
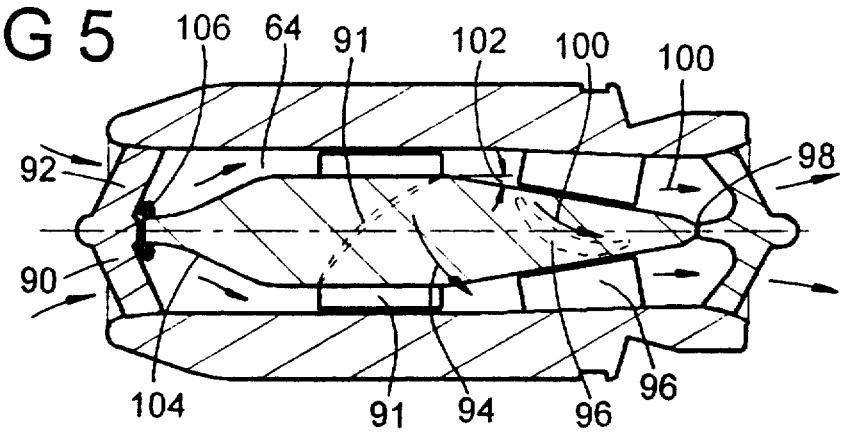
Figure 6:
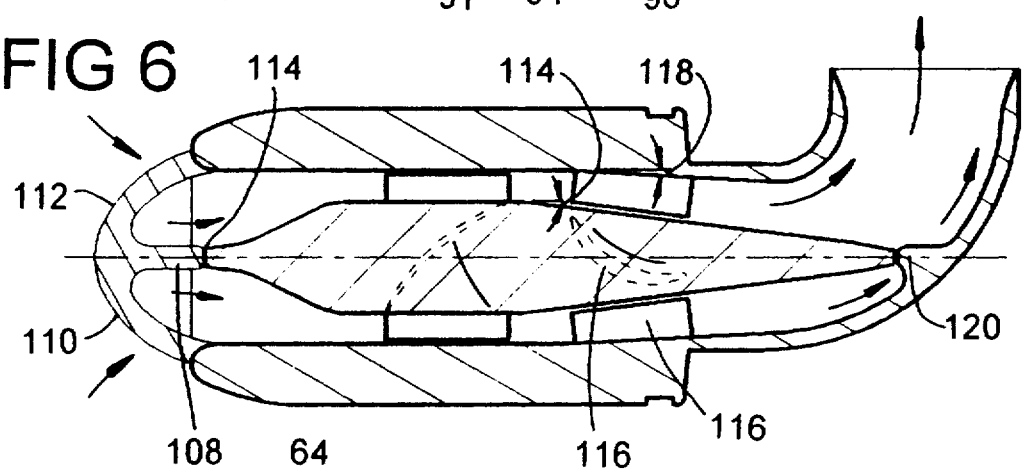
Figure 15:
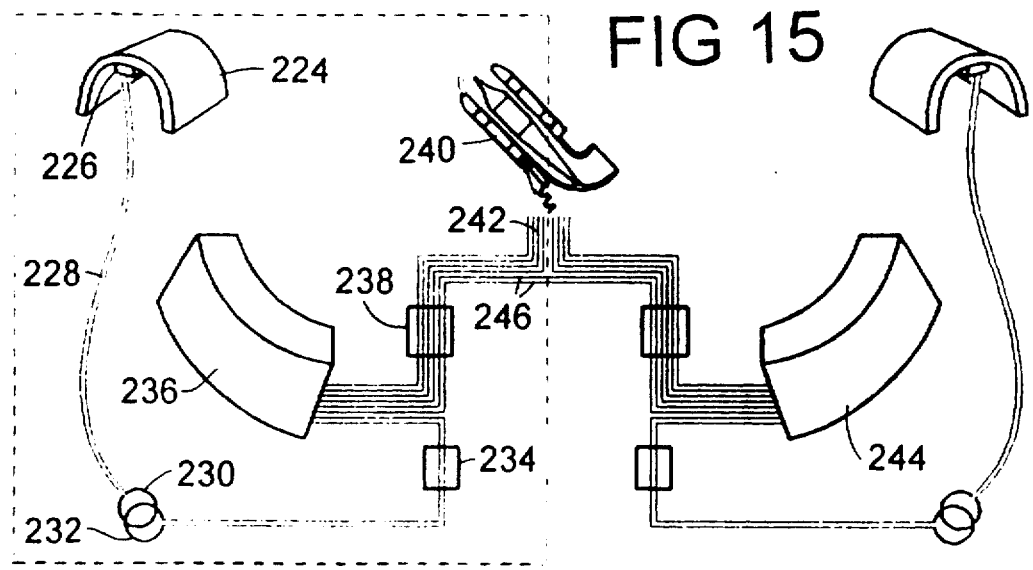
Figure 22:
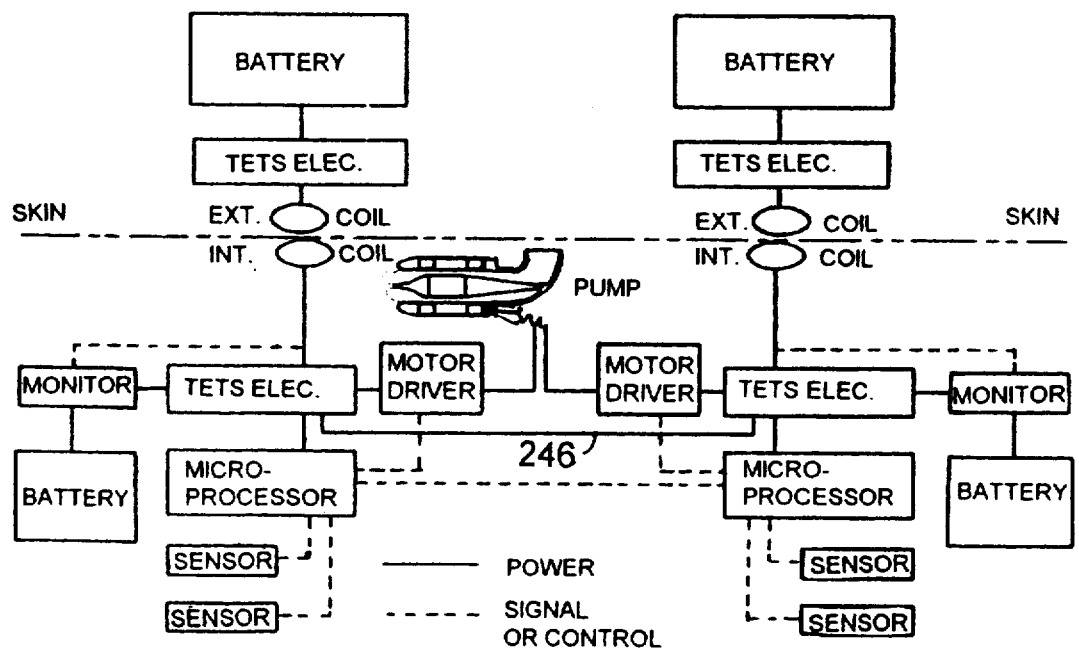

FIGS. 20 & 21 are longitudinal views of metal bellows electrical conduits having rigid tubular segments interposed between flexible metal diaphragms.

Figure 22:
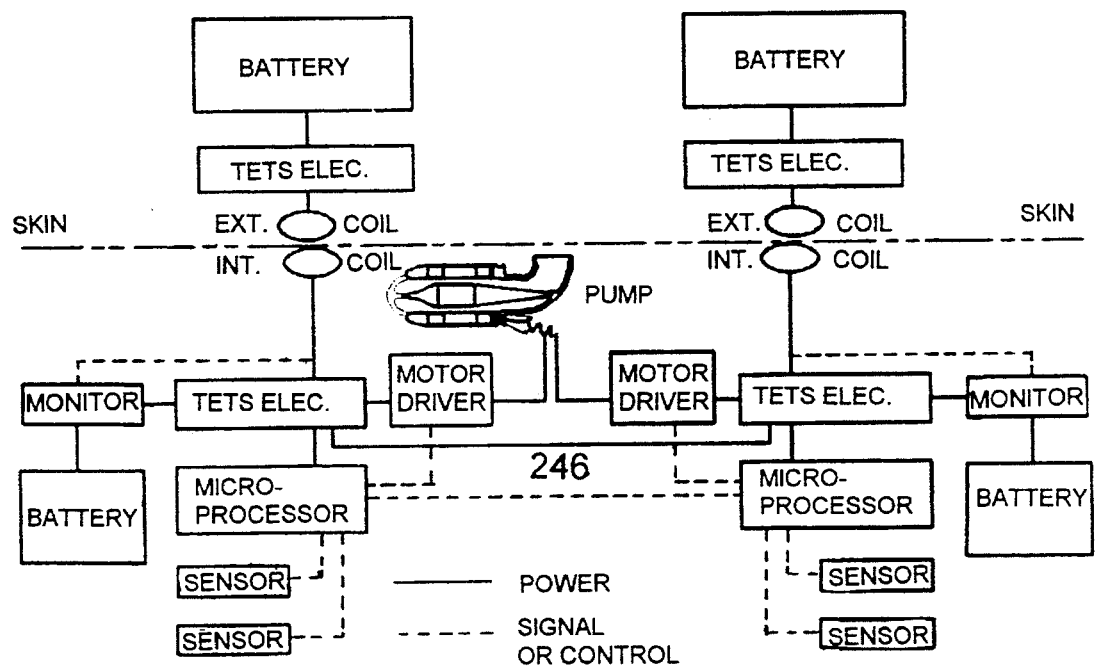

FIG. 22 is a block diagram of the redundant electronics system.

SPECIFIC DESCRIPTION OF THE INVENTION

The life of the patient depends on the safety of the entire system which achieves extraordinary reliability by providing maximum backup capability. Complete electrical redundancy assures that the pump will continue to run despite failure of any electrical component. In the event of mechanical failure a valve is provided which prevents back flow so that the natural heart can effectively sustain the life of the patient until the system can be surgically replaced. Safety not only means avoidance of failure of the device to pump blood but also the system must remain free of infection, and be supported by the body without damage to any organs or tissues, under the stress of the continual flexing and motion during normal activity. The individual component design must be optimized, and also the integrated function of the system is a major aspect of the current invention.

The Overall System

Figure 1:
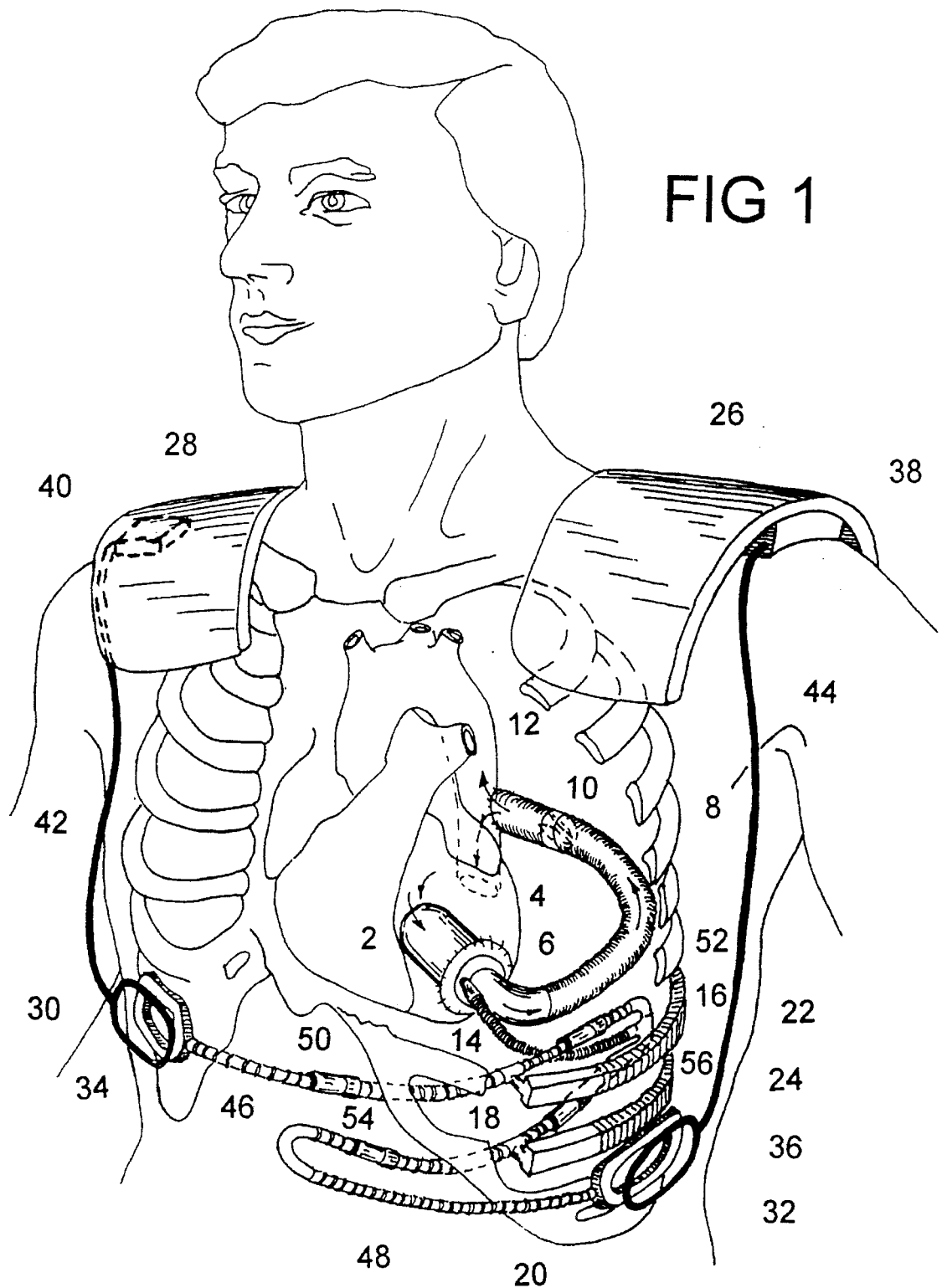
FIG. 1 is a schematic drawing of the complete system indicating the position of the components.

FIG. 1 illustrates the complete system. The intraventricular pump 2 is attached into the left ventricle 4 by sewing cuff 6. Blood enters it from the left ventricle and is pumped through the outflow graft 8 and through the valve 10 into the aorta 12. The pump is driven by an electric motor which has two separate sets of windings powered by two separate sets of motor wires. Both of these sets of wires pass through a metal bellows conduit 14, are separated at a "T" connector 16, and connect to one of two implanted electronics modules 18 and 20 contained within rib-shaped metal enclosures 22 and 24. These also contain rechargeable batteries with enough energy storage to power the device for about an hour when it is disconnected from any external power source. The rib shaped electronics and battery modules may be corrugated to permit them to be bent at surgery to conform to the individual curvature of the patient's rib cage. They typically are fabricated from titanium alloy (Ti-6Al-4V) and may have a textured surface such as sintered titanium microspheres to promote tissue ingrowth and prevent infection.

Power for the system is provided by two externally worn rechargeable batteries 26 and 28, which may be high-capacity flexible polymer lithium-ion cells or other suitable types. These together typically provide 8–12 hours of power and are worn on a vest which is typically changed 2–3 times per day. The vest itself, which is not shown in the drawing for clarity, incorporates fasteners such as velcro or zippered pouches, which removably retain the batteries in proper position. Alternatively, the vest may locate the batteries generally at the waist rather that the shoulders. The vest includes fasteners to removably retain two power transmitter coils 30 and 32 in proper position adjacent to two internal receiver coils 34 and 36 implanted under the skin. Proper alignment of the internal and external coils, in addition to being generally maintained by the vest, may be further secured by means of mating permanent magnets (not shown) configured to both hold the external coil against the skin and to position it. Each external battery pack includes an electronics module 38 and 40 which include monitoring and alarm devices as well as the necessary electronics for battery charging and power transmission to the transmitter coils. The external cables 42 and 44 are typically sealed waterproof polymer cables which require no connectors. Power to charge the external batteries is delivered via the coils 30 and 32 as electromagnetic energy from a charging unit (not shown). The method of providing power across the intact skin via transmitter and receiver coils is well known in the literature and is referred to as TETS for Transcutaneous Energy Transmission System. In the present invention, redundant TETS systems are employed and the overall system is designed such that each external battery can provide power to both internal electronics modules via either one of the two sets of TETS coils. This permits one external coil at a time to be removed without loss of external power which protects the skin between the coils from damage due to unrelieved excessive pressure. Powder from each of the internal TETS coils 34 and 36 is conducted to the two respective internal power modules 18 and 20 by wires within metal bellows conduits 46 and 48. Hermetically sealed internal connectors 50, 52, 54, and 56 are provided to facilitate surgery and to permit replacement of any module of the system without replacement of the other components.

Another embodiment of the system utilizes direct electrical connection of external battery and control systems to the pump within the patient by means of a cable that penetrates the skin. This is referred to as percutaneous power transmission. The percutaneous embodiment has the advantage that no batteries or electronics other than the motor need be implanted within the patient. The redundant sets of motor wires are each connected to a separate external electronics control system and battery supply. In the event of failure of any component, the module containing it can easily be replaced without surgery. The wires are brought across the skin within a metal bellows conduit which is coated with a porous layer to promote tissue ingrowth and wound healing. This constitutes the percutaneous lead. Once outside the body, a "T" connector is used to separate the two sets of motor coils to two electronics systems. External waterproof connectors are,provided to permit the batteries to be changed. While one battery is disconnected to change it, the other battery continues to power the pump. In the percutaneous embodiment, an internal connector is provided so that, in the event of a skin infection, a new percutaneous cable may be implanted at a different location, and the infected cable removed without changing the pump.

The Axial Flow Pump

Figure 2:
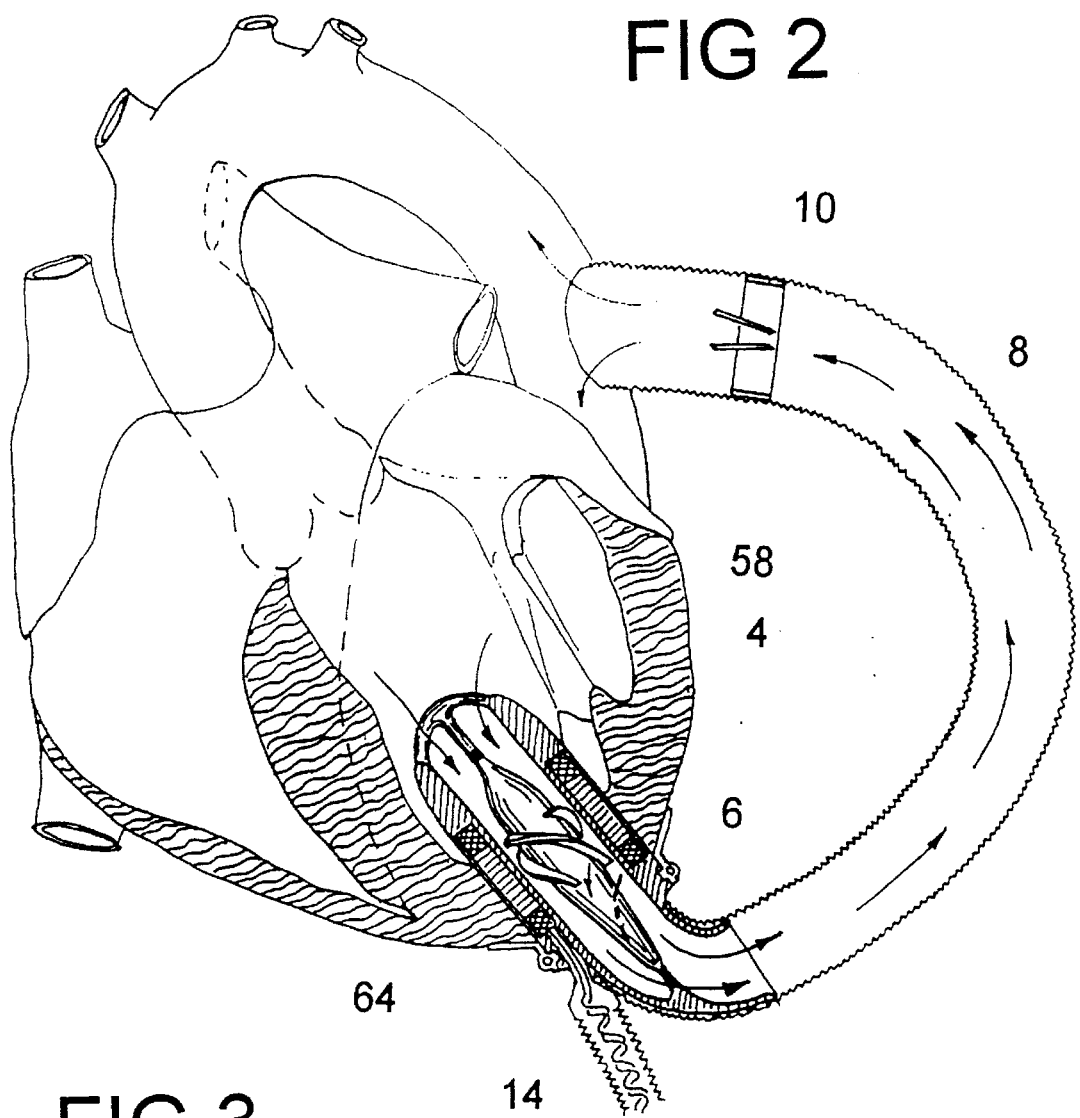
FIG. 2 is a drawing of an intraventricular axial flow pump in the heart.
Figure 3:
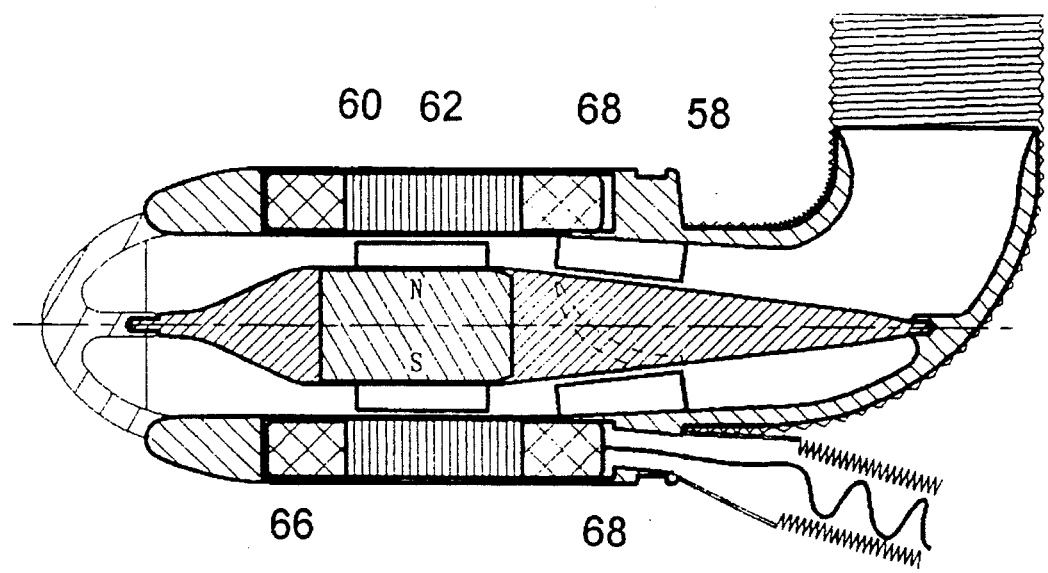
FIG. 3 is a longitudinal section of the blood pump showing the motor, bearing, and hydrodynamic blade positions.

FIGS. 2 and 3 show the axial flow pump implanted at the left ventricular apex (FIG. 2) and a close-up view of the device (FIG. 3). The pump housing 58 is retained by sewing cuff 6 with the motor 60 and pump impeller 62 inside the heart. The pump rotor 64, which contains the magnet of the motor 66, spins within the motor bore, and is isolated from blood contact by a thin-walled titanium sleeve which lines the inside of the motor bore. FIG. 3 best illustrates the preferred embodiment of the pump. Blood is entirely isolated from the motor cavity 68, by welded seams of the pump assembly, and likewise the rotor magnet is completely enclosed in a titanium shell with welded seams to exclude blood.

Figure 4:
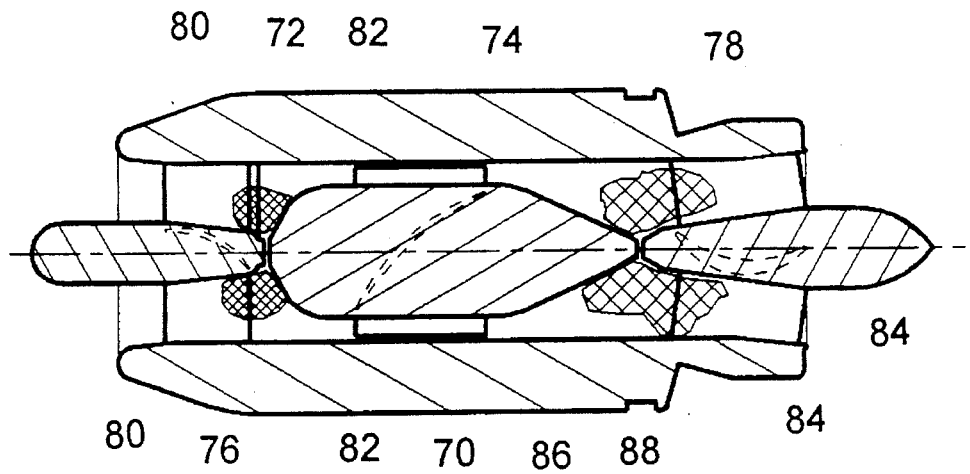
FIG. 4 is a longitudinal section of one pump configuration showing much pump thrombus at both the inflow and the outflow sides of the rotor.
Figure 5:
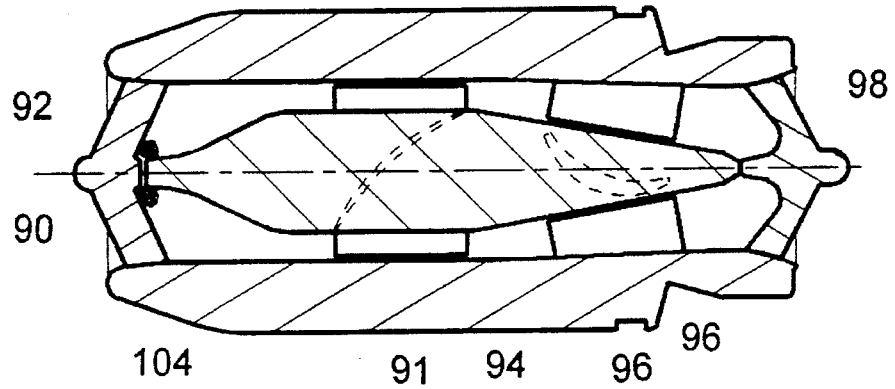
FIG. 5 is a longitudinal section of an improved configuration showing a small thrombus at the inflow side of the rotor.
Figure 6:
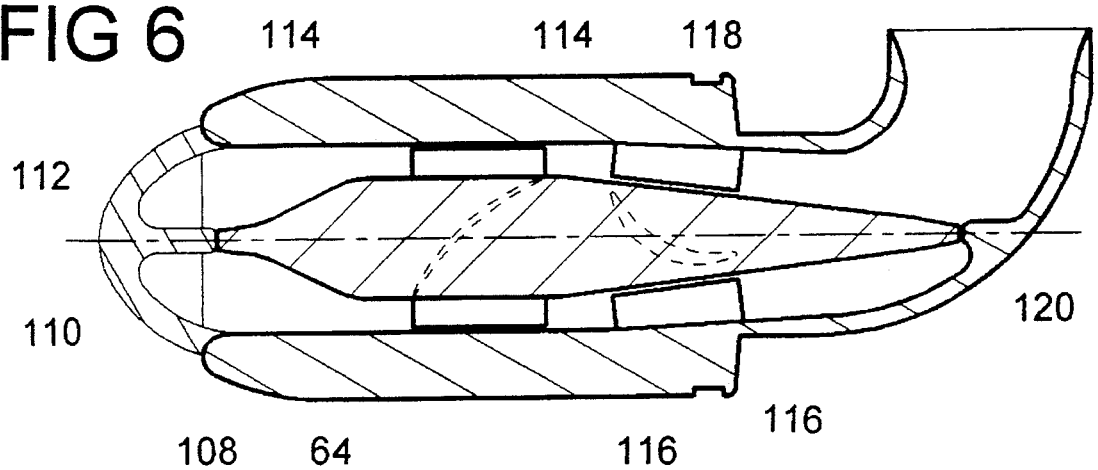
FIG. 6 is a longitudinal section of further improved configuration showing no thrombus at either end of the rotor.

My previous U.S. Pat. No. 4,994,078 disclosed the principle of high-flow washing of the rotating and stationary components of the pump to prevent thrombus accumulation. Experience has demonstrated that additional principles not previously recognized or disclosed in the prior art may be specifically incorporated in axial flow blood pumps to enhance washing of these junctions and reduce thrombus within the pumps. The present invention provides an improved pump structure. FIGS. 4, 5, and 6 are Scale drawings of actual pump flow path geometries tested in animals. The pump of FIG. 4 utilized a rotor 70 having a blunt leading profile 72 and a steep hub outflow angle 74 of 24 degrees. After four months of use in a calf, this pump rotor seized due to thrombus 76 at the inflow side and thrombus 78 at the outflow side of the rotor. The inflow thrombus 76 was due a flow stagnation region around the inflow side bearing and the outflow thrombus 78 was due to a combination of factors. The pump blades included inflow stators 80, impeller blades 82, and outflow stators 84. Arrow 86 indicates the rotational component of the fluid flow leaving the impeller. Due to the steep angle of the impeller hub in this region of the pump, flow separation with a rotating eddy at 88 in the region of the outflow bearing occurred. Thus the junction of the rotating and stationary components of the pump at the outflow side was not in a region of high flow but was within a relatively stagnant portion of an eddy. The pump of FIG. 5 completely eliminated thrombus at the outflow bearing as demonstrated in a five-month animal implant. No inflow stators are included but rather there are two inflow bearing support struts 90 and 92. The impeller 91 imparts about the same rotational flow to the blood indicated by arrow 94 as did the impeller of the pump of FIG. 4. However, outflow stator blades 96 placed between the impeller and the outflow side bearing 98 redirect the rotational component of the flow to the axial direction as indicated by arrows 100 before the flow passes across the outflow bearing. Additionally, the outflow side of the rotor was designed with a flat taper angle 102 of only about 10 degrees to prevent flow separation. Thus there was neither flow separation nor a rotational eddy around the outflow bearing. It was well washed by high flow and therefore remained free of thrombus although it was exactly the same bearing design as used in the pump of FIG. 4. The inflow side of the pump rotor of FIG. 5 was gradually tapered at 104 to avoid a flow stagnation area like at 72. However, a small thrombuos 106 still formed at the inflow bearing junction because this junction was located in a flow stagnation region downstream from the bearing support struts 90, and 92.

FIG. 6 illustrates a design which provides high flow across both the inflow and outflow bearings without stagnant eddies or fluid swirl around the bearings. This model pump is presently implanted in an animal which is not clinically anticoagulated and the device has functioned perfectly for more than three months at the time of submission of this patent application. We expect both the inflow and outflow junctions of the rotating and stationary parts of the pump to remain free of thrombus indefinitely. The inflow bearing is supported by a post extending axially from support struts 110 and 112. Thus the junction 114 at the inflow bearing is kept out of the flow stagnation region in the lee of the support struts. The rotor hub outflow side angle is even flatter—only 6 degrees—and the outer walls of the flow channel around the outflow stators 116 are also tapered at an angle 118 to further suppress flow Separation. The outflow bearing is washed by a high-flow stream of axially flowing blood and is supported by a streamlined strut 120 projecting from the titanium wall of the pump.

The experimental findings of thrombus formation within the pump relate to the design of the flow channels and blades and not only to the washing of the junctions between the rotating and stationary components of the device. Although it is well known that turbulence, flow separation, and stagnation are detrimental to pump performance in general, the design of a permanent blood pump having blood-immersed bearings presents special problems related to the fact that the blood-clotting system, including thrombus formation and platelet properties, acts to form an adhesive system evolved to glue wounds together. This will also bind bearings if the surface area of the bearing is too great in relation to the forces applied to rotate them. Very small diameter bearings have the advantage of low surface area which limits the adhesive force of blood clotting. If the bearing diameter is minimized, the diameter of the magnets necessary to rotate the impeller must be considerably larger. If the magnets are placed within the hub of a rotor carrying the impeller, there must be a taper on both ends of the hub if the blood-flow path is to wash directly across the bearings. If it does not there will be a crevice where clot will form. The design of the flow path around that taper is important. In the pump design of FIG. 4, thrombus formed at both ends of the rotor in relation to the taper of the rotor hub. If the flow channel between the outflow side of the impeller and the outflow bearing increases in cross-sectional area too abruptly, the blood flow will separate and may form sufficiently stagnant eddies to clot. This appears to have occurred in the pump of FIG. 4. The flow channel in this pump increases by more than 50% between the impeller and the outflow bearing over a short axial length. Positioning the stators between the impeller and the outflow bearings in the designs of FIGS. 5, 6, and 7 permits gradual taper to the hub and prevents a rotating eddy around the bearing. In the pump of FIG. 5 the cross-sectional area of the flow channel between the impeller and the outflow stators increases only 17% and in the pump of FIG. 6 only the area increases by only 10%.

FIG. 7 shows a generalized axial flow blood pump in which both inflow stators 122 and outflow stators 124 are provided. A rotor 126 with an impeller 128 is supported at both the inflow and outflow ends by support struts 130 and 132 which hold blood-immersed bearings at 134 and 136. Magnets (not shown) which rotate the rotor may be supported by the impeller blades or may be located within the hub of the rotor. The important feature of this design is that the blood stream washing across both the inflow and outflow bearings is substantially axial. Rotational fluid flow is confined to the region of the pump between the inflow and outflow stators.

The Bearings

Figure 8:
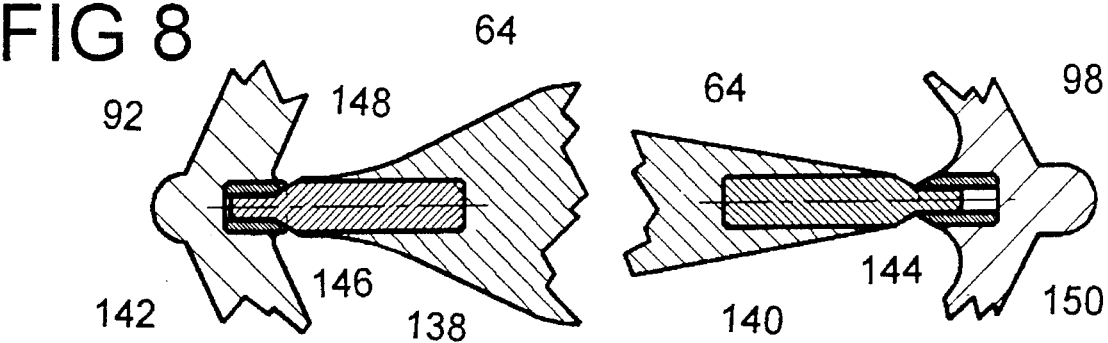
FIG. 8 is a longitudinal section of the bearing details of a design as shown in FIG. 5.

FIG. 8 shows the inflow and outflow bearings utilized with pumps of the designs illustrated in FIGS. 4, 5, and 6. The rotor 64 supports two rotating ceramic bearing members 138 and 140. Each of these has a cylindrical shaft portion 142 and 144 which supports radial load. The inflow rotating bearing member 138 has a tapered surface 146 which mates with a similarly tapered surface of the stationary ceramic inflow bearing sleeve 148. Axial thrust load is born by contact at these tapered surfaces. The tapered surface has two advantages. First, it is self-centering and contributes to radial load bearing capacity when thrust load is applied. Second, it provides a greater surface area to carry thrust load than bearings of the same diameter that are not tapered. This reduces the load per unit of surface area and reduces wear.

The object is to obtain the highest load-bearing capacity at the smallest diameter to minimize surface rubbing speed, heat generation, and binding by blood adhesive properties. The inside bore of sleeve 148 is only slightly larger than the diameter of the shaft rotating within it. Typical radial clearance is a few ten-thousandths of an inch between the rotating bearing shaft pins 142 and 144 and the stationary ceramic sleeves 148 and 150 held by support struts 92 and 98. The diameter of the pins is typically 0.037" and thus in a pump typically operating at 10,000 RPM the bearing pin surface speed is only about 1.6 feet/second. The bearings are preferentially made of a very hard, wear-resistant ceramic having high thermal conductivity and high fracture toughness. The best material available to date appears to be a sintered silicon carbide material containing titanium diboride, although other materials can also be used. Using this material, in a five month animal study, wear measurements have indicated less than 0.000013" of wear on the thrust-bearing surfaces and less than 0.00005" radial wear on the shaft and bore Surfaces. This extremely low wear is expected to permit the design to operate reliably for more than a decade.

Figure 9:
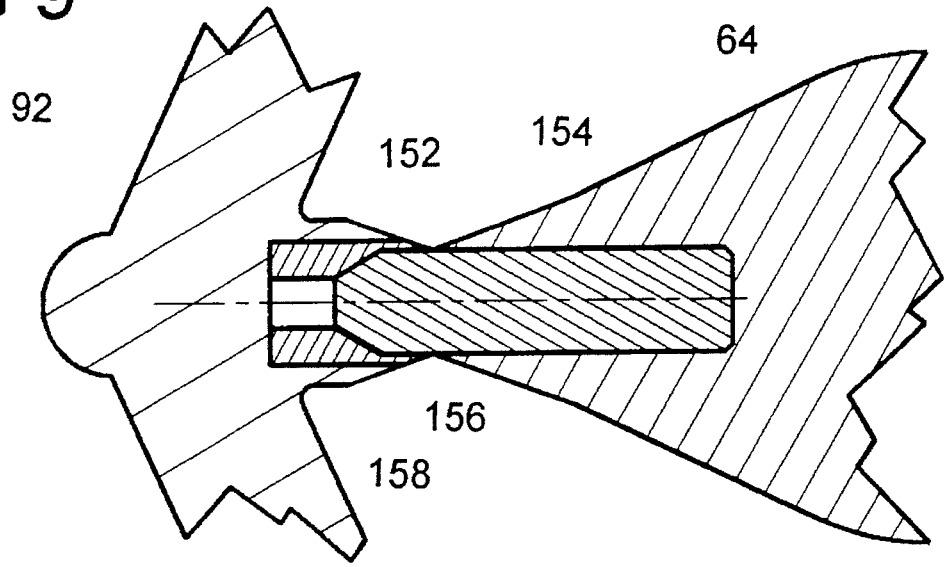
FIG. 9 is a longitudinal section of the inflow side of a thrust and radial bearing design.

FIG. 9 illustrates another bearing design in which a tapered thrust-bearing surface 152 on the end of a rotating bearing pin 154 is combined with a radial load supporting cylindrical surface 156. The stationary bearing sleeve 158 is mounted into the support strut 92.

Figure 10:
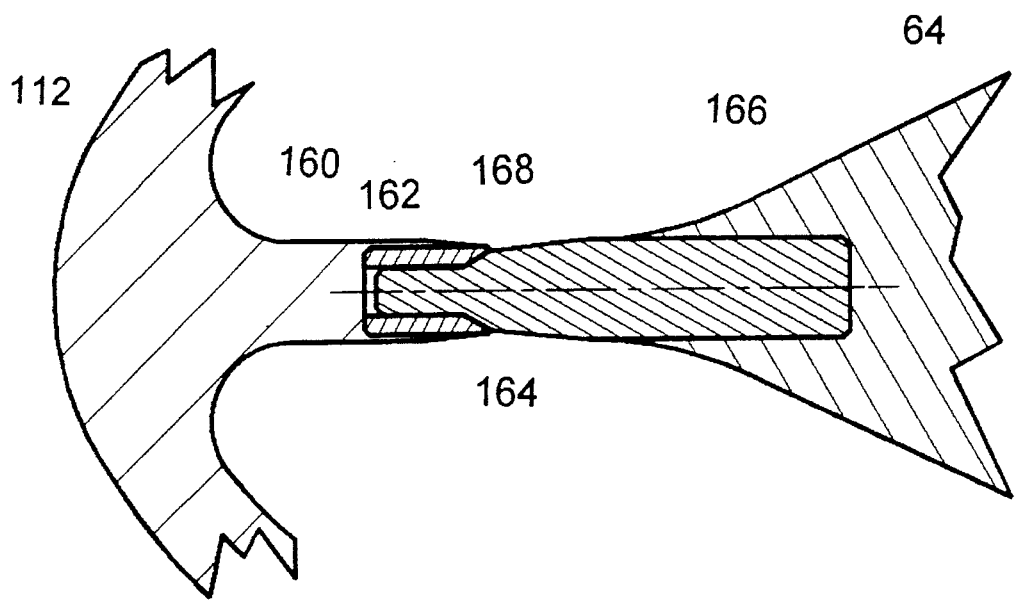
FIG. 10 is a longitudinal section of the inflow bearing configuration of the preferred embodiment pump shown in FIG. 3.

FIG. 10 shows the preferred embodiment of the inflow bearing and support for optimal high blood flow washing and avoidance of thrombus. An extension post 160 extending from the inflow support strut 112 holds the stationary ceramic inflow bearing sleeve 162. A tapered thrust-bearing surface 164 is provided which mates with a similar surface on the rotating bearing member 166. The junction of the rotating and stationary parts at 168 is designed to minimize the crevice present. The extension post 160, holds the bearing away from the support strut 112 so that the junction 168 is not in an area of flow stagnation downstream of the strut. The structure provides excellent axial blood flow across the bearing for both mechanical washing and optimal dissipation of heat generated by bearing friction.

The Motor

Reliability of the system is enhanced by providing motor redundancy. FIG. 11 shows a motor in which two separate armatures 170 and 172 are mounted about a single rotor 174 containing a motor magnet 176. Two separate sets of motor wires 178 and 180 power two sets of motor coils within each armature, and it is readily apparent that power need be applied to only one set of wires and coils in order for rotor 174 to be rotated. Thus, if any wire were to break while both sets of coils were operative, the motor would continue to run powered by the unaffected armature. If this general arrangement is utilized in a brushless DC motor the rotational positions of the coils in each armature must be set in proper position to assure the optimal motor torque. A motor having two separate sets of motor coils within one armature has the advantage that the proper alignment of both sets of coils is assured. FIG. 12 illustrates the winding arrangement of a simple brushless DC motor. A stack of laminations 182 has three teeth 184, 186, and 188, and three slots 190, 192, and 194. The motor magnet is shown at 196. In this three-phase design, coils 198, 200, and 202 are wrapped around the teeth with the wires lying in the slots. Only one coil is wrapped around each tooth. Referring to the coil 202 wrapped around tooth 188, there are two ends of the wire 206, and 208. One of these is connected to ground and the other is intermittently connected to the power source with proper timing for commutation depending on the rotary position of the magnet. The ground wires from all three coils may be joined together to a common lead wire and thus four lead wires may be used to power the motor as represented by the four wires in the set 178 (in FIG. 11). FIG. 13 illustrates one tooth of a motor lamination set like that of FIG. 12 having a different arrangement of windings to accomplish the motor redundancy. Two coils 212 and 214 are wrapped around tooth 210, rather than one coil as in the motor of FIG. 12. Similarly, two coils are wrapped around each of the other motor teeth. With proper connection and the use of two common leads (a separate common for each set of coils) two sets of motor wires are provided, each of which is sufficient to power the motor. FIG. 14 illustrates a motor of this design, having a total of eight motor leads 216 and only one armature 218. Actually, two sets of four leads each 220 and 222 are provided. Depending on the number of motor phases and type of connections used, differing numbers of wires may be provided in each set. The essential principle is that two complete sets of motor coils and leads are provided.

Interconnection of System Components

Figure 15:
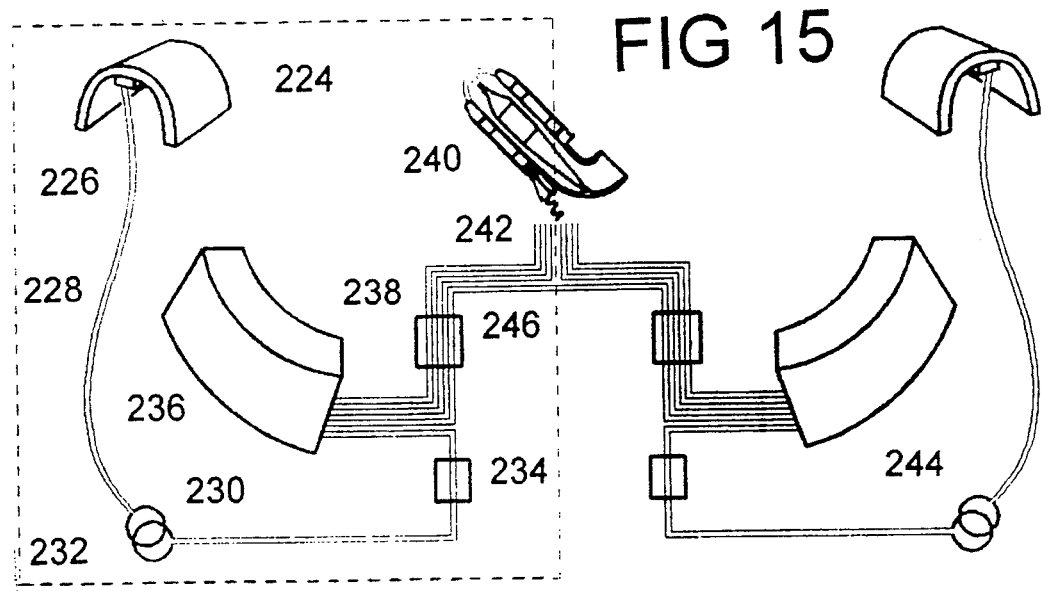
FIG. 15 is a schematic diagram of the electrical connections of the components of the system.
Figure 16:
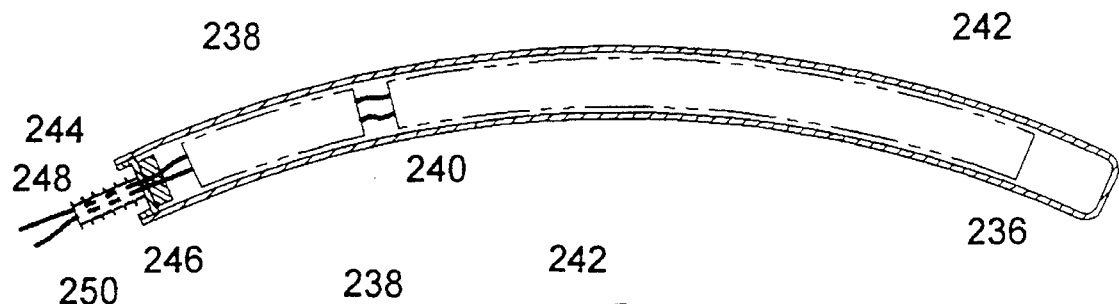
FIG. 16 is a longitudinal section of a generally rectangular rib-shaped metal case containing electronics and batteries.

A highly redundant embodiment of the invention utilizing dual electronics and battery systems with a motor of the type illustrated in FIG. 14 and a transcutaneous energy transmission system (TETS) is shown in FIG. 15. The dotted line on the left encloses one set of components, and the second set is shown on the right. The external battery 224 is connected to the external electronics module 226 which is connected via cable 228 to the external TETS coil 230. This external subsystem is removable from the patient. The internal TETS coil 232 is connected via an implantable connector 234 to the internal electronics and battery module 236 contained in a rib-shaped enclosure. This module is connected via another implantable connector 238 to both the blood pump motor 240 via a four wire cable 242 and to the other implantable electronics and battery system 244 via a two-wire cable 246. FIG. 16 shows the interconnection of the components within the rib shaped case 236. The electronics system 238 is connected by wires 240 to the battery 242, also shown in FIG. 17. A metal cover 244 is welded to case 236 at 246 to effect a hermetic seal. The wires interconnecting the electronics to the other components outside the enclosure pass through a metal bellows conduit 248 which is welded to the case at 250. The other end of the metal bellows is hermetically bonded to a ceramic core of an implantable connector through which pass hermetically sealed wire feedthroughs.

The Cables

The implanted power cables are subject to frequent bending with motion of the patient. The use of metal bellows enclosures protects the wires from corrosive contact with body fluids. To further assure long-term durability, multi-stranded coiled wires are used, as has proven successful with pacemaker wires. The metal bellows conduits are preferentially made of titanium alloy, as is all of the exposed metal surface of the implanted components. FIG. 19 illustrates a typical standard metal bellows design in which multiple formed washer-like diaphragms are welded together to form a flexible tubular structure. In this type of design deep grooves 304 are present which become very narrow channels on the inside curvature of the bellows when it bends. These crevices are not well-exposed to vascularized tissue, and are subject to infection if bacteria or other organisms are present. FIG. 20 shows a welded bellows conduit specifically configured to avoid deep narrow crevices even when the bellows bends. The conduit is composed of a multiplicity of short tube segments 306, 308, and 310 welded to pairs of diaphragms 312, 314, and 316 to form a continuous hermetically sealed tube. Only very shallow crevices 318 and 320 are present. The tubes may first be coated with titanium microspheres before welding to provide a porous surface for tissue ingrowth. FIG. 21 shows a further improvement on this principle which eliminates the crevices entirely while maintaining good flexibility of the bellows conduit. Bellows subunits 22, 324, and 326 are each fabricated from a single piece of metal and have diaphragm portions at each end 328 and 330, and tube-like segments 332 between them. These subunits are welded at the outside periphery of the diaphragm portions 334 and 336 to form the hermetic seal. The subunits may be coated with sintered titanium microspheres in a fluidized bed at high temperature before being welded together. This provides an excellent textured outside surface for tissue ingrowth to further prevent infection. Alternatively, the segments may be first welded together and then coated with microspheres.

The Electronics and Control System

FIG. 22 is a block diagram of the electronics system, which is composed of four subsystems. These include two external electronics and battery modules, which are each separately removable from the patient for recharging or service, and two implanted electronics and battery modules, which may be disconnected and replaced surgically. The system is designed for high reliability utilizing redundancy and high reliability components. Two separate TETS systems are provided which permits the patient to remove one at a time while remaining on external power. An interconnection 246 between the two internal electronics system and associated switching is provided to connect the power received from either internal TETS coil to either internal electronics system where it may be used to recharge the internal batteries, directly power the blood pump, or both.

The Batteries

Many types of batteries could be used and as future battery technology improves more options will become available. The presently preferred battery system uses polymer lithium-ion flat sheet cells which are stacked or folded in multiple layers. In the rib configuration, the individual battery layers are not bonded together which makes the stack flexible because as the rib-shaped case is bent to match the curvature of the individual patient, the layers slide against one another. Dry lubricant, such as teflon powder, may be placed between the layers to prevent them from sticking. The external battery also may also use dry lubricant between the layers to achieve a more flexible battery pack. Present polymer lithium-ion batteries developed by Bellcore have an energy density of 95–120 watt hours/kg. Using this type of batteries within two ribs of proper size to fit most patients, and based on the power requirements of the pumps tested to date, enough energy storage is provided in two "ribs" to operate the pump for about 2–3 hours under nominal conditions. The batteries may be recharged about 2000 times. Thus, if the patient disconnects from the external batteries for two hours each day, 2000 recharge cycles will provide about 2000/365=5.5 years before the batteries need to be replaced. To extend this time and provide a system which will function for a decade without reoperation, the electronics system includes control which alternately draws power from one battery and, the next time the system is operated for more than five minutes on battery power, uses the other battery. By this method, the patient may briefly remove the vest to change it without the system recognizing this as a period of significant internal battery discharge. The patient is instructed not to use battery power for more than one hour each day. Thus the system times for changing the battery vest) uses first one battery and then the other on alternate days. The system permits the internal batteries to function for 10–11 years without requiring surgical replacement, and all throughout this time period the patient has the benefit of both batteries being functional, rather than one battery being worn out during years 6–11 as if it had only been used during the first 6 years while the other was left unutilized.

The Physiologic Control System

The internal systems are each provided with a microprocessor and sensors which detect the physiological condition of the patient and adjust the pump motor speed accordingly. The microprocessor systems also provide additional programmable motor speed control, such as the use of a variable speed cycle to open and close the valve in the outflow graft, to provide pulsatility, or to adjust the pump output for the proper levels for large vs. small patients. These functions may programmed via a telemetry link from an accessory external computer such as a pocket sized PC (not shown) which may utilize the TETS coils for data transfer. Information may be transferred from the external computer to the external electronics system (located with the batteries) using a wireless method in the infrared or other electromagnetic spectrum. As an alternative to telemetry in the case of percutaneous systems the PC may be plugged into a connector and be interconnected with the external battery pack electronics system to act as the overall system command unit. The pocket controller may contain the system alarms, battery charge status indicators, liquid crystal display, and input buttons. The following is example of one control method.

Patient A is a 130-lb. individual with a history of hypertension and myocardial infarction in NYHA class IV failure. His ejection fraction measured at catheterization prior to the device implant was 17%. In this patient, a programmed control regime is selected based on his body weight and poor myocardial function. The programmed regime sets pump speed for three levels of exercise (lying down, sitting, and walking) which are recognized by the system's sensors. These speeds correspond to the appropriate flow at the differential pressure across the pump estimated for the patient. In this example, the flow lying down determined by the program regime will be 3–4 l/min., the flow sitting will be 4–5 l/min., and the flow walking will be 5–7 l/min. Based on measurements of the patient's aortic pressure, and an estimate of the mean ventricular pressure, the pump differential pressure estimate is determined and the motor speed necessary to achieve the desired flow range is calculated. This may be, for example, 7,200 RPM lying, 8,400 RPM sitting, and 10,500 RPM walking. Assume the patient is lying down. The motor Speed will be 7,200 RPM. Flow will be generally in the 3–4 l/min. range but will not be determined precisely. When the patient stands up and begins to walk, the system sensors will recognize this and the motor speed will be automatically increased to 10,500 RPM. Flow will increase to the 5–7 l/min. range. Then, when the patient sits down, the sensors will recognize this and speed will automatically be reduced to 8,400 RPM, reducing flow to 4–5 l/min.

The information disclosed in the description of the present invention is intended to be representative of the principles that I have described. It will thus be seen that the objects of the invention set forth above and those made apparent from the preceding description are efficiently obtained and that certain changes may be made in the above articles and constructions without departing from the scope of the invention. It is intended that all matter contained in the above description or shown in the accompanying drawings shall be interpreted as illustrative but not in a limiting sense. It is also understood that the following claims are intended to cover all of the generic and specific features of the invention herein described and all statements of the scope of the invention which as a matter of language might be said to fall there between.

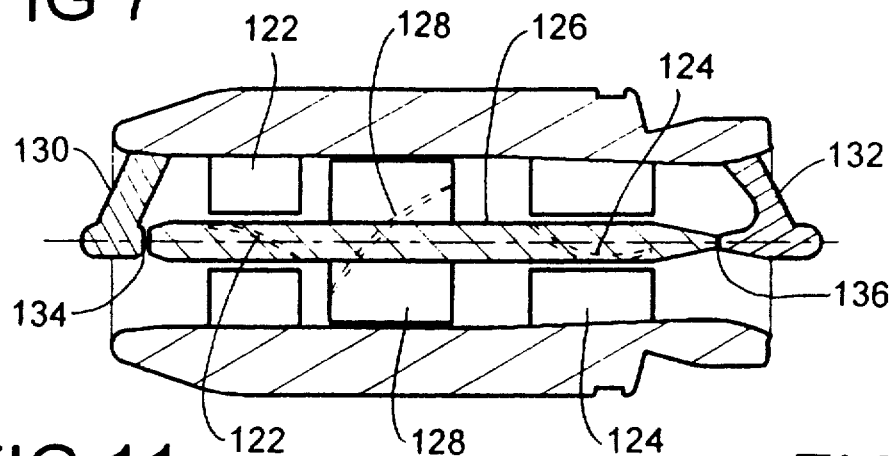
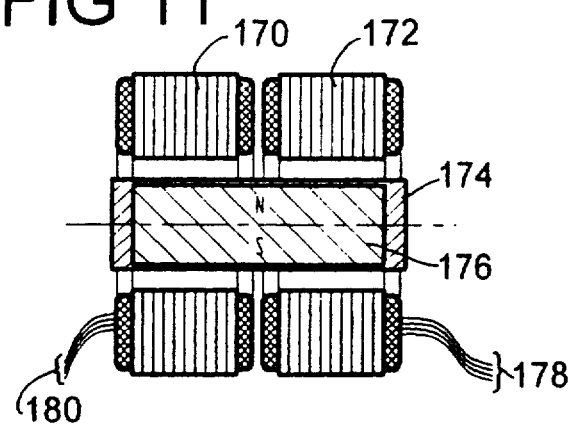
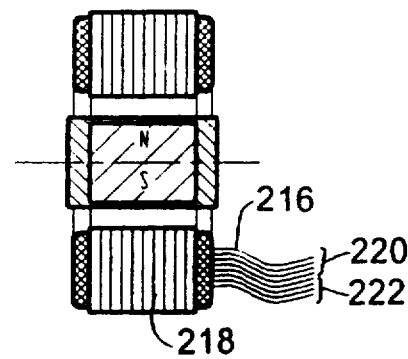
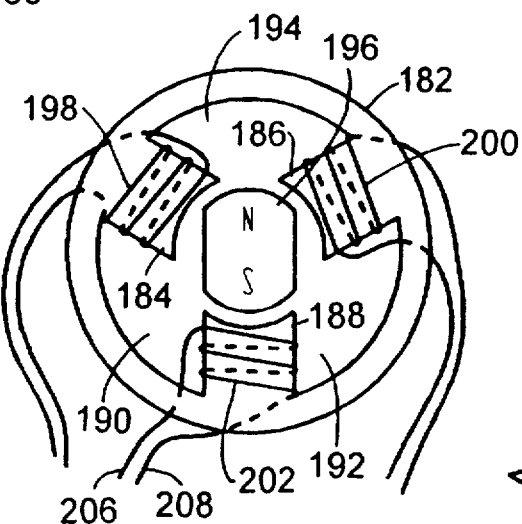
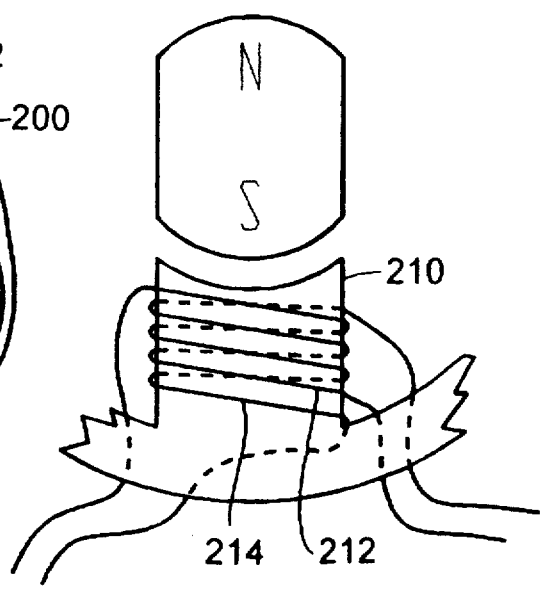

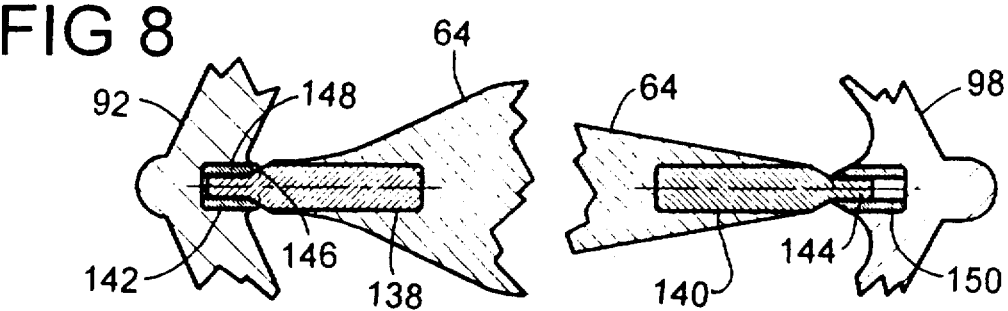
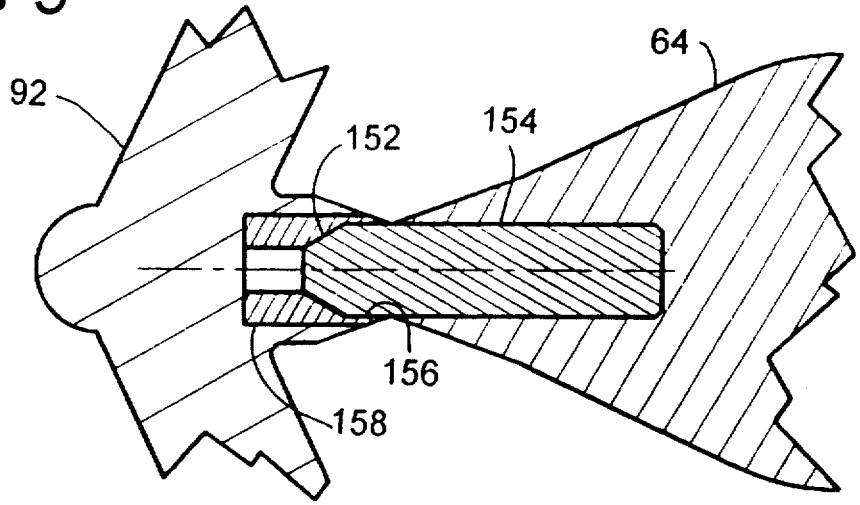
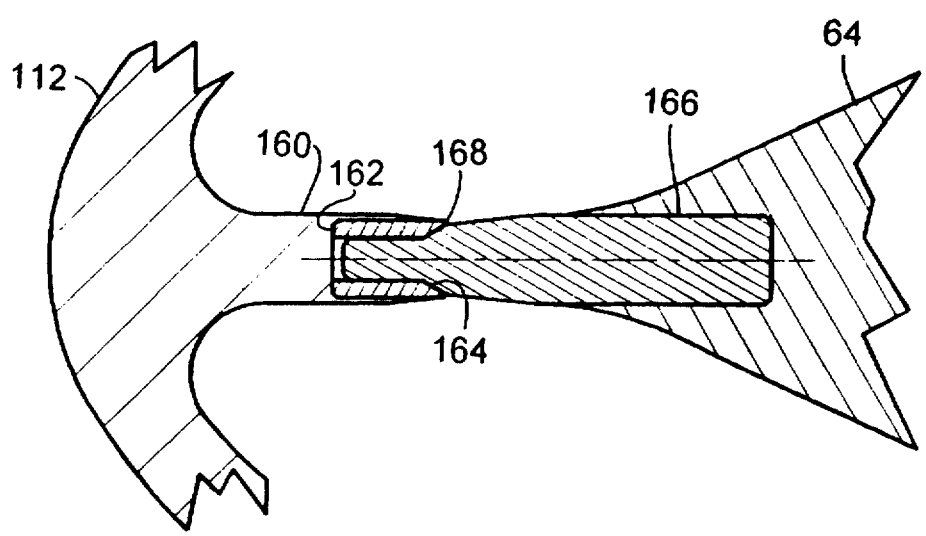

Figure 17:
FIG. 17 is a schematic illustration of the electronics and batteries for fit into the case illustrated in FIG. 16.
Figure 18B:
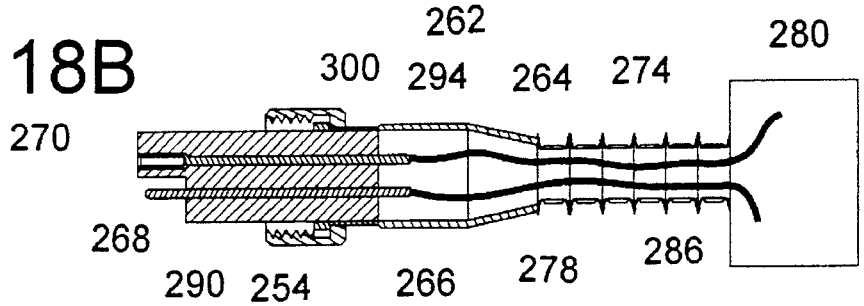

FIG 16
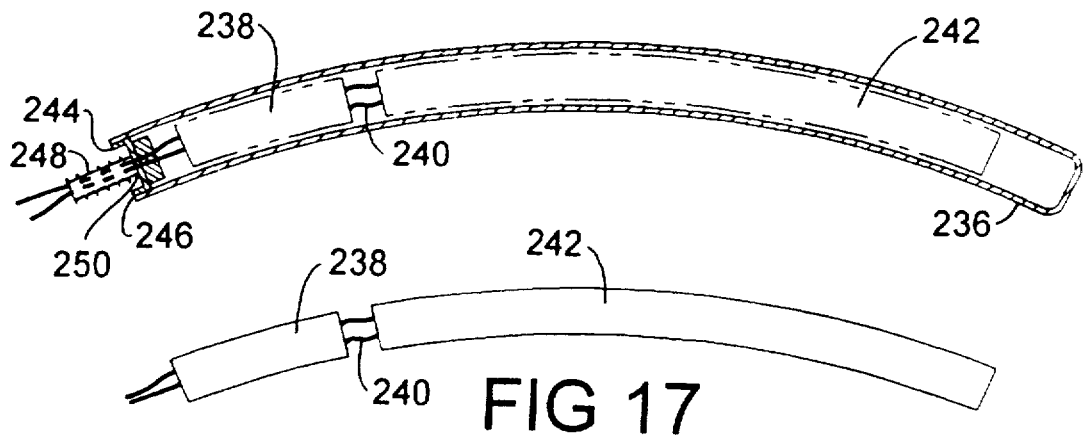
FIG 17
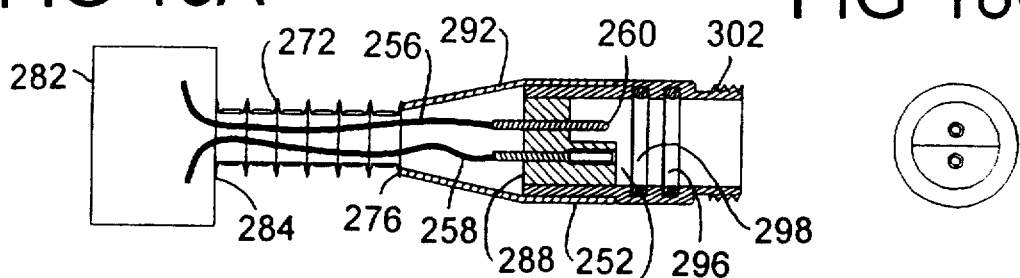
FIG 18A
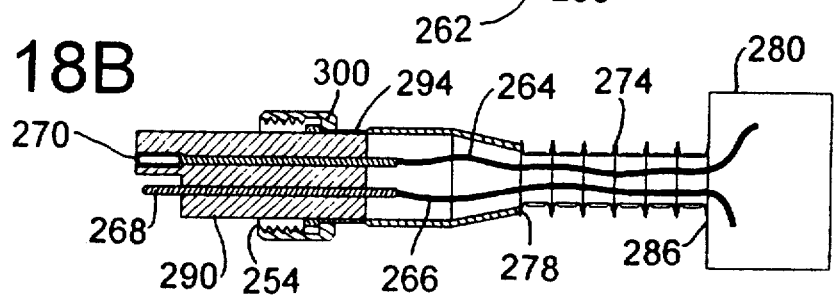
FIG 18C
FIG 18B
FIG 19
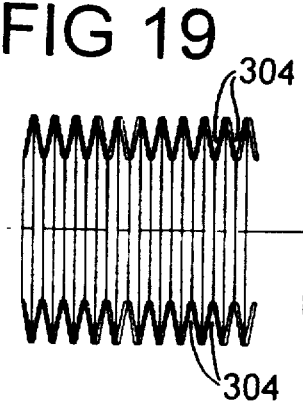
FIG 20
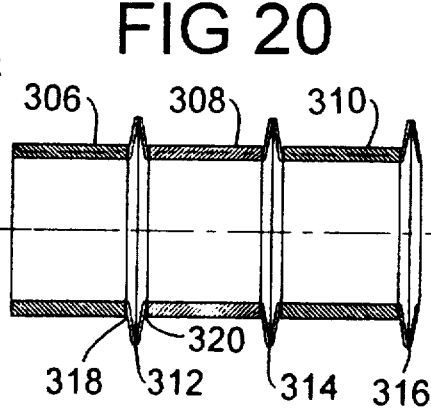
FIG 21
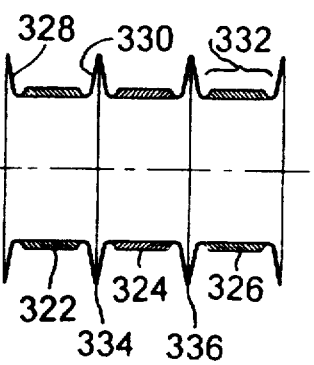

I claim:

1. A high reliability blood pumping system comprising:
   a. an electric motor having a single rotor;
   b. blood pumping means actuated by the single rotor of the electric motor;
   c. electric motor armature means having first and second sets of motor coils configured such that either set of coil provides sufficient electromagnetic force to rotate said rotor and actuate said blood pumping means;
   d. first and second electronic power systems to respectively supply electrical energy to said first and second sets of motor coils with the proper communication timing, said first and second power systems respectively wired to said first and second sets of motor coils such that power to rotate said rotor and operate said blood pumping means may be provided by either of said first and second power systems and associated set of motor coils, wherein in the event of failure of either set of motor coils or power systems, said blood pumping means will continue to run driven by the remaining set of motor coils or power system.

2. The blood pumping system of claim 1 including monitoring and control means interconnecting said first and second power systems to permit said first power system to supply electrical energy to said second set of motor coils sufficient to operate said blood pumping means and to permit said second power system to supply electrical energy to said first set of motor coils sufficient to operate said blood pumping means, in the event of failure of either set of said motor coils or said power systems.

3. The blood pumping system of claim 1 in which said blood pumping means comprise an axial flow, mixed flow or centrifugal flow pump.

4. A high reliability cardiac assist system comprising:
   a. an electrically powered blood pump;
   b. dual electronics and battery systems capable of powering and controlling said blood pump, and being adapted to be implanted within a patient;
   c. dual transcutaneous energy transmission systems, each having a set of coils comprised of an external transmitter coil and a receiver coil adapted to be implanted within a patient, each set capable of providing power to either of said dual implanted electronic and battery system such that one of said external transmitter coils can be removed without discontinuing power transmission by the other; and
   d. an external battery system, capable of providing power to said implanted electronics and battery systems via either or both of said transcutaneous power transmission systems.

5. The high reliability cardiac assist system of claim 4 in which said blood pumping means comprise an axial flow, mixed flow or centrifugal flow pump.

6. A high reliability hydrodynamic blood pump cardiac support system utilizing residual function of the natural heart as an emergency backup comprising;
   a. a hydrodynamic blood pump including inflow and outflow conduit means for connection between the left ventricle and aorta or between the right ventricle and pulmonary artery;
   b. a valve in said outflow conduit means preventing back-flow into the ventricle in the event said pump stops; and
   c. pump control system means adapted to vary the pump flow so as to cause said valve to close and open periodically at a frequency sufficient to prevent thrombosis due to stagnation of blood around the valve.

7. The high reliability hydrodynamic blood pump cardiac support system of claim 6 in which said blood pump is adapted to be implanted within the natural heart.

8. An electrically powered blood pump, comprising;
   a. Electric motor means including stationary windings and permanent magnet rotor means;
   b. Two bearings supporting both ends of said rotor means to permit rotation of said rotor means around a rotational axis thereof, one of said bearings located on the inflow side of said rotor means and the other of said bearings located on the outflow side of said rotor means, each said bearing adapted to be immersed in blood;
   c. A generally tubular conduit extending through said motor windings and defining an annular blood channel between said motor windings and said permanent magnet rotor means;
   d. hydrodynamic pump impeller means mounted upon said rotor means within said tubular conduit;
   e. An elongated, generally conical tapered hub of said rotor means maintained within said conduit and extending from the vicinity of said impeller means to said bearing on the outflow side of said rotor means, said tapered hub having an outer surface defining an angle of taper less than or about equal to 10 degrees relative to the rotational axis; and
   f. Stationary outflow stator blade means affixed to the inside of said tubular conduit and extending inward therefrom, such that said stator blade means redirects the rotational component of the blood flow produced by said impeller means towards a generally axial direction before said flow passes across the other of said bearings on the outflow side of said rotor means.

9. An axial blood pump rotor and blade structure adapted to provide optimal washing of bearings which support said rotor, comprising;
   a. a housing having a generally tubular channel through which blood flows;
   b. an elongated rotor mounted for rotation within said housing and having an inflow end and an outflow end;
   c. first bearing support means upstream of said rotor, said first support means supporting inflow bearing means;
   d. at least one pump impeller blade mounted upon said rotor and defining an inflow side and an outflow side;
   e. said elongated rotor defining an elongated rotor hub disposed between said outflow side of said impeller and said outflow end of said rotor;
   f. second bearing support means downstream of said rotor, said second support means supporting outflow bearing means;

g. at least one stationary outflow stator blade fixed to an inner wall of said housing through which the blood is pumped and axially located between said impeller and said outflow bearing means, said outflow stator blade configured to redirect the rotational component of the fluid flow stream exiting the impeller to a generally axially direction before the flow stream crosses said outflow bearing means; and h. a pump flow channel within said housing comprised of the spaces between said housing, said rotor, said first and second bearing support means and said inflow outflow bearings, configured such that, under the operating conditions of the pump, turbulence, flow separation, and flow stagnation sufficient to cause failure of the pump due to thrombus formation is prevented.

10. The axial flow blood pump of claim 9 in which the cross-sectional area of said pump flow channel at an upstream edge of said outflow stator blade is no more than 20% greater than the cross sectional area at said outflow side of said impeller blade.

11. The axial flow blood pump of claim 9 in which said rotor is tapered at each end to a diameter ⅓ or less than the maximum rotor diameter.

12. The axial flow blood pump of claim 9 in which said first bearing support means includes a stationary bearing sleeve at the end of an axially extending generally cylindrical post of said housing said cylindrical post being no more than 20% larger in diameter than the outside diameter of said bearing sleeve, and the axial length of said post being at least twice its diameter.

13. An apparatus for pumping blood, which comprises:

a) a housing having an inflow opening and an outflow opening, and defining a blood path for blood to flow from the inflow opening to the outflow opening;

b) a rotating member disposed within the housing and mounted for rotational movement within the blood path, the rotating member including an impeller blade for imparting pump energy to blood through the blood path;

c) a first bearing mounting the rotating member, the first bearing disposed adjacent the outflow opening;

d) a second bearing mounting the rotating member, the second bearing disposed upstream of the first bearing; and e) an outflow stator blade disposed between the impeller blade of the rotating member and the first bearing.

14. The apparatus according to claim 13 further including a drive mechanism for imparting rotational movement to the rotating member.

15. The apparatus according to claim 14 wherein the drive mechanism includes an electric motor, the electric motor having stationary windings and a rotor magnet, the rotor magnet incorporated within the rotating member.

16. The apparatus according to claim 13 wherein the outflow stator blade is configured and dimensioned to direct blood flowing through the blood path across the first bearing.

17. The apparatus according to claim 16 wherein the rotating member has an outflow portion defining a generally tapered configuration.

18. The apparatus according to claim 16 wherein the housing member and the rotating member define a generally annular space therebetween, the blood path including the annular space.

19. The apparatus according to claim 16 further comprising a second bearing disposed adjacent the inflow opening for mounting the rotating member.

20. The apparatus according to claim 19 including an inflow stator blade extending from the housing and being disposed between the at least one impeller blade of the rotating member and the second bearing.

21. The apparatus according to claim 19 wherein the second bearing includes a tapered thrust bearing surface, the tapered thrust bearing surface cooperating with a correspondingly dimensioned thrust-bearing surface associated with the rotating member to facilitate thrust load bearing capacity of the second bearing.

22. The apparatus according to claim 21 wherein the second bearing includes a radial load supporting surface, the radial load supporting surface disposed toward the outflow opening and adapted to facilitate radial load bearing capacity of the second bearing.

23. An apparatus for pumping blood, which comprises:

a) a housing having an inflow opening and an outflow opening, and defining a blood path for blood to flow from the inflow opening to the outflow opening;

b) a rotating member disposed within the housing and mounted for rotational movement within the blood path, the rotating member including an impeller blade for imparting pump energy to blood through the blood path and having an outflow portion defining a generally streamlined tapered configuration;

c) a first bearing mounting the rotating member, the first bearing disposed adjacent the outflow opening; and d) an outflow stator blade extending from the housing member and being configured and dimensioned to direct blood flowing through the blood path axially across the first bearing.

24. An apparatus for pumping blood, which comprises:

a) a housing having an inflow opening and an outflow opening and defining a blood path for blood to flow from the inflow opening to the outflow opening;

b) a rotating member mounted for rotational movement about a rotational axis within the blood path of the housing, the rotating member including an impeller blade for imparting pumping energy to blood passing through the blood path, the rotating member having an outflow portion defining a generally tapered configuration, the tapered configuration defining an angle of inclination with respect to the rotational axis less that than about 10°; and c) a drive mechanism for imparting rotational movement to the rotating member.

25. The apparatus according to claim 24 wherein the rotating member is supported for rotational movement by a first bearing disposed adjacent the outflow opening and a second bearing disposed adjacent the inflow opening.

26. The apparatus according to claim 25 wherein the outflow portion of the rotating member is disposed between the impeller blade and the second bearing.

27. An apparatus for pumping blood, which comprises:

a) a housing having an inflow opening and an outflow opening and defining a blood path for blood to flow from the inflow opening to the outflow opening;

b) a rotating member disposed within the blood path, the rotating member including an impeller blade for imparting pumping energy to blood flowing through the blood path, the rotating member supported by inflow and outflow support struts and mounted for rotational movement by a first bearing associated with the outflow support strut and a second bearing associated with the inflow support strut, the inflow support strut having an axial post extending generally axially therefrom supporting the second bearing such that the juncture of the second bearing and the rotating member is disposed along the blood path a sufficient distance beyond said inflow support strut to be away from any local area of flow stagnation downstream of the strut and thus to prevent the accumulation of thrombus at the juncture; and c) a drive mechanism for imparting rotational movement to the rotating member.

28. The apparatus according to claim 27 wherein the rotating member has outflow and inflow bearings mounted thereto, the inflow and outflow beatings respectively mating with the first and second bearings.

29. The apparatus according to claim 28 wherein the outflow and inflow bearings each includes axial and tapered load-bearing surfaces, and wherein the first and second bearings each include corresponding axial and tapered surfaces in mating contact with the axial and tapered load bearing surfaces of the respective outflow and inflow bearings.

30. The apparatus according to claim 29 wherein the axial load bearing surfaces of the outflow and inflow bearings are remotely disposed from the rotating member with relation to the tapered load bearing surfaces.

31. The apparatus according to claim 29 wherein the tapered load bearing surfaces of the outflow and inflow bearings are remotely disposed from the rotating member with relation to the axial load bearing surfaces.

32. An apparatus for pumping blood, which comprises:

a) a housing having an inflow opening and an outflow opening and defining a blood path for blood to flow from the inflow opening to the outflow opening;

b) a rotating member disposed within the housing and mounted for rotational movement within the blood path by a station try inflow beating disposed adjacent the inflow opening and a stationary outflow bearing disposed adjacent the outflow opening, the inflow and outflow beatings each including an axial load bearing surface and tapered load bearing surfaces, the axial and tapered load bearing surfaces cooperating and mating with corresponding axial and tapered load bearing surfaces associated with the rotating member to thereby enhance thrust load bearing capacity thereof, the rotating member having an impeller blade to impart pump energy to blood along the blood path; and c) a drive mechanism for imparting rotational movement to the rotating member.

33. The apparatus according to claim 32 wherein the rotating member has first and second rotatable bearings mounted thereto respectively mating with the stationary outflow and inflow bearings, the first and second rotatable bearings defining the axial and tapered load bearing surfaces associated with the rotating member.

34. The apparatus according to claim 32 wherein the axial load bearing surfaces of the outflow and inflow bearings are remotely disposed from the rotating member with relation to the tapered load bearing surfaces.

35. The apparatus according to claim 32 wherein the tapered load bearing surfaces of the outflow and inflow bearings are remotely disposed from the rotating member with relation to the axial load bearing surfaces.

36. An apparatus for pumping blood, which comprises:

an electric motor with a rotor;

a blood pumping member actuated by the rotor;

a first electronic and power system including a first set of motor armature coils and associated battery for powering the electric motor to rotate the rotor and actuate the blood pumping member;

a second electronic and power system including a second set of motor armature coils and associated battery for powering the electric motor to rotate the rotor and actuate the blood pumping member; and the first electronic and power system operable simultaneously with the second electronic and power system, each of the first and second electronic and power systems capable of individually operating the electric motor to actuate the blood pumping member such that in the event of failure of either the first or second electronic and power systems, the electric motor and blood pumping member will continue to operate driven by the remaining electronic and power system.

* * * * *

UNITED STATES PATENT AND TRADEMARK OFFICE
CERTIFICATE OF CORRECTION

Page 1 of 8

PATENT NO. : 5,613,935
DATED : March 25, 1997
INVENTOR(S) : Robert Jarvik

It is certified that error appears in the above-identified patent and that said Letters Patent is hereby corrected as shown below:

Drawings:

Delete Drawing Sheets 1-21, and substitute therefor the Drawing Sheets, consisting of Figs. 1-21, as shown on the attached pages.

Signed and Sealed this

Twenty-first Day of April, 1998

Attest:

BRUCE LEHMAN

Attesting Officer     Commissioner of Patents and Trademarks